United States Patent
Acharya et al.

(10) Patent No.: US 10,932,701 B2
(45) Date of Patent: Mar. 2, 2021

(54) NON-INVASIVE BIO-FLUID DETECTOR AND PORTABLE SENSOR-TRANSMITTER-RECEIVER SYSTEM

(71) Applicant: THE JOHNS HOPKINS UNIVERSITY, Baltimore, MD (US)

(72) Inventors: Soumyadipta Acharya, Baltimore, MD (US); William Chen, Lino Lakes, MN (US); Phillip J. Oh, Hillsborough, NJ (US); Judy C. Doong, San Jose, CA (US); Noah Lampel Greenbaum, Watchung, NJ (US); Guilherme Barros, Towaco, NJ (US); George Major Chen, Hacienda Heights, CA (US); David Yin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 585 days.

(21) Appl. No.: 14/388,913

(22) PCT Filed: Mar. 28, 2013

(86) PCT No.: PCT/US2013/034361
§ 371 (c)(1),
(2) Date: Sep. 29, 2014

(87) PCT Pub. No.: WO2013/149011
PCT Pub. Date: Oct. 3, 2013

(65) Prior Publication Data
US 2015/0164396 A1    Jun. 18, 2015

Related U.S. Application Data

(60) Provisional application No. 61/617,545, filed on Mar. 29, 2012.

(51) Int. Cl.
   *A61B 5/1455*    (2006.01)
   *A61B 5/145*    (2006.01)
   *A61B 5/00*    (2006.01)

(52) U.S. Cl.
   CPC ........ *A61B 5/14546* (2013.01); *A61B 5/0004* (2013.01); *A61B 5/1455* (2013.01);
(Continued)

(58) Field of Classification Search
None
See application file for complete search history.

(56) References Cited

U.S. PATENT DOCUMENTS

| | | | | |
|---|---|---|---|---|
| 4,651,741 A | * | 3/1987 | Passafaro | A61B 5/14535 356/41 |
| 2002/0049389 A1 | * | 4/2002 | Abreu | A61B 3/1241 600/558 |

(Continued)

*Primary Examiner* — Eric F Winakur
*Assistant Examiner* — Marjan Fardanesh
(74) *Attorney, Agent, or Firm* — Harrity & Harrity, LLP

(57) ABSTRACT

The present invention is directed to a bio-fluid detector such as a hemoglobin detector having the capability of receiving, storing and transmitting health information utilizing a portable transmitter and receiver including electronic PDAs such as cell phones. Further, the present invention utilizes a non-invasive hemoglobin detector that is connected to a portable transmitter-receiver such as PDAs including, but not limited to, cell phones.

20 Claims, 6 Drawing Sheets

(52) U.S. Cl.
CPC .......... *A61B 5/6826* (2013.01); *A61B 5/6828* (2013.01); *A61B 5/6838* (2013.01); *A61B 5/6898* (2013.01); *A61B 5/7228* (2013.01); *A61B 2560/045* (2013.01)

(56) References Cited

U.S. PATENT DOCUMENTS

| | | |
|---|---|---|
| 2004/0102687 A1 | 5/2004 | Brashears et al. |
| 2004/0260161 A1 | 12/2004 | Melker et al. |
| 2007/0073128 A1 | 3/2007 | Hoarau et al. |
| 2008/0001735 A1 | 1/2008 | Tran |
| 2009/0069648 A1* | 3/2009 | Irazoqui .................. A61B 3/16 600/302 |
| 2009/0163784 A1* | 6/2009 | Sarpeshkar ........ A61B 5/14551 600/322 |
| 2009/0171170 A1* | 7/2009 | Li .......................... A61B 5/00 600/301 |
| 2009/0240125 A1* | 9/2009 | Such ................ A61B 5/14552 600/323 |
| 2009/0326386 A1* | 12/2009 | Sethi ...................... A61B 5/021 600/480 |
| 2011/0137141 A1* | 6/2011 | Razoumov ........... A61B 5/0002 600/316 |
| 2012/0016219 A1 | 1/2012 | Fujii |
| 2014/0073887 A1* | 3/2014 | Petersen .............. A61B 5/0015 600/323 |

\* cited by examiner

NON-INVASIVE BIO-FLUID DETECTOR AND PORTABLE SENSOR-TRANSMITTER-RECEIVER SYSTEM

CROSS-REFERENCE TO RELATED APPLICATIONS

This application is a 35 U.S.C. § 371 U.S. national entry of International Application PCT/US2013/034361, having an international filing date of Mar. 28, 2013, which claims the benefit of U.S. Provisional Application No. 61/617,545, filed Mar. 29, 2012, the content of each of the aforementioned applications is herein incorporated by reference in their entirety.

GOVERNMENT LICENSE RIGHTS

This invention was made with government support under NIH R21 EB015638 awarded by the National Institutes of Health (NIH). The government has certain rights in the invention.

FIELD OF THE INVENTION

The present invention relates generally to medical screening. More particularly the present invention relates to a device and method for determining hemoglobin levels in blood.

BACKGROUND OF THE INVENTION

Anemia is a condition of having a low amount of red blood cells or hemoglobin content in blood, resulting in an impaired ability of the blood to transport oxygen. Moderate to severe anemia is particularly dangerous during pregnancy for both the mother and the baby. 100,000 maternal deaths and 600,000 neonatal deaths worldwide are attributable to anemia each year. The prevalence of anemia in the developing world is staggering, with estimates by the WHO of up to 50% among pregnant women and 65% among children. Of these, there is a subgroup of severely anemic pregnant women who are particularly at risk for life-threatening complications during gestation and especially during birth; moderate-severe anemia is associated with higher risk of perinatal complications such as post-partum hemorrhage, a major cause of maternal death. In total, anemia is estimated to be a direct or indirect cause of 26% of maternal deaths in India. In addition to this toll, millions of infants worldwide are affected by maternal anemia through morbidities ranging from low birth weight, failed lactation, neonatal sepsis, to impaired cognitive development.

Over the past few decades, a number of developing nations, particularly India, have conducted programs of state sponsored iron and nutritional supplementation. The efficacy of these programs has not been well documented and the benefits they provide are often the subject of debate. The reason for this dearth of clear benefits is unclear. One possible factor is a lack of compliance among those at risk, caused by the fact that most cannot be screened for anemia and are thus unaware of the severity of their condition and the need for supplementation, and also by the lack of anemia education and the marketing of an effective public health message involving iron supplementation.

One crucial step towards improving compliance and efficacy of anti-anemia programs is the implementation of a system to track the progress of a given intervention by the large-scale collection of hemoglobin levels of pregnant women. There is thus a need for a device that is able to be used widely and cheaply to screen for anemia, with the aim of reinforcing existing programs in India and other nations by identifying those at the highest risk, especially those with moderate-severe anemia in late gestation, in order to bring them "out of the cold" and into existing healthcare structures. Moreover, if able to track patient data geographically and over time, such a device would facilitate macro-scale public health policy by enabling the targeting of health care initiatives to areas in need and by providing feedback on interventions. Finally, such a system would increase the accountability of the programs, allowing for more efficient application of limited resources.

The current standard of care for anemia detection includes the clinical pallor test and the WHO color scale. Blood based assays are only performed at equipped laboratories and hospitals, well out of reach of the average citizen of a developing nation. As a result, few are screened at all, and those who are, are screened by methods that are not sufficiently objective. The noninvasive pallor test is based on the color of the conjunctiva tissue of the eye, relying on the judgment and experience of the healthcare worker, which is often limited, in order to determine whether or not the patient has anemia.

The WHO color scale is an invasive test that requires a drop of blood be placed on a special piece of paper and dried. The color is then compared to a reference swatch. This test is also quite variable depending on the environmental conditions (lighting, humidity) in which the test is performed, and the results are again subject to variable judgment and experience. Moreover, the test is invasive and introduces discomfort and the risk of infection.

Pulse oximeters are well known in the art. The theory behind hemoglobin detection is based on the absorbance of light by hemoglobin in the blood. Pulse-oximetry based hemoglobin meters use 7+ wavelengths to detect concentrations of all species of hemoglobin, including methemoblogin and carboxyhemoglobin, to company stated accuracies of +−1 g/dL. While these types of devices are highly accurate they are not adaptable to lay users and are often cost prohibitive and overly complex for implementation in developing nations as a screening tool. While there are known scientific attempts made at pulse-oximetry based hemoglobin detection, these attempts achieved better accuracy than required for the purposes of use in developing nations and at far greater cost and complexity.

Frequency modulation based communication between a sensor and a smart phone are known in the art. The Project Hijack device, designed by students at the University of Michigan, is aimed at the iPhone™ and iPad™, and uses a frequency based analog to digital conversion method to communicate with the phone. The phone is then able to decode this frequency based digital signal. The disadvantage of this is the complexity of circuitry in their design and of the frequency modulation scheme.

It would therefore be advantageous to provide a device that reduces the variability of the standard of care in an easy to use, cost-effective manner.

SUMMARY

According to a first aspect of the present invention a system for determining hemoglobin level in a subject's blood includes a mobile communication device and a sensor system. The sensor system includes a light emitting diode (LED) configured to transmit light through tissue of the subject. A photosensor is configured to receive and measure light transmitted through the tissue of the subject by the LED. Additionally, a communications board is configured to trigger the LED to transmit light, configured to receive information related to the light received by the photosensor, and further configured to communicate with the mobile communication device.

In accordance with an aspect of the present invention, the system also includes an LED driver and a timer coupled to the LED driver. A power source is included for providing power to the sensor system and can take the form of a battery or the mobile communication device. The communication board further comprises an amplifier, and the amplifier can take the form of an AM or BFSK device. The mobile communication device can take the form of a cellular telephone that has a headset-in jack and a headset-out jack. The LED can take the form of two LEDs. A wavelength of light emitted by a first LED of the two LEDs can be 660 nm and a wavelength of light emitted by a second LED of the two LEDs can be 810 nm.

In accordance with another aspect of the present invention, a sensor system for detecting hemoglobin in a subject's blood includes a finger clip configured to be disposed on a fingertip of the subject. The system also includes a light emitting diode (LED) configured to transmit light through tissue of the subject and disposed on a first surface of the finger clip adjacent to the fingertip of the subject. Additionally, the system includes a photosensor configured to receive and measure light transmitted through the tissue of the subject by the LED and disposed on a second surface of the finger clip opposite the first surface of the finger clip. A communications board is configured to trigger the LED to transmit light and configured to receive information related to the light received by the photosensor.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

Figure 1:
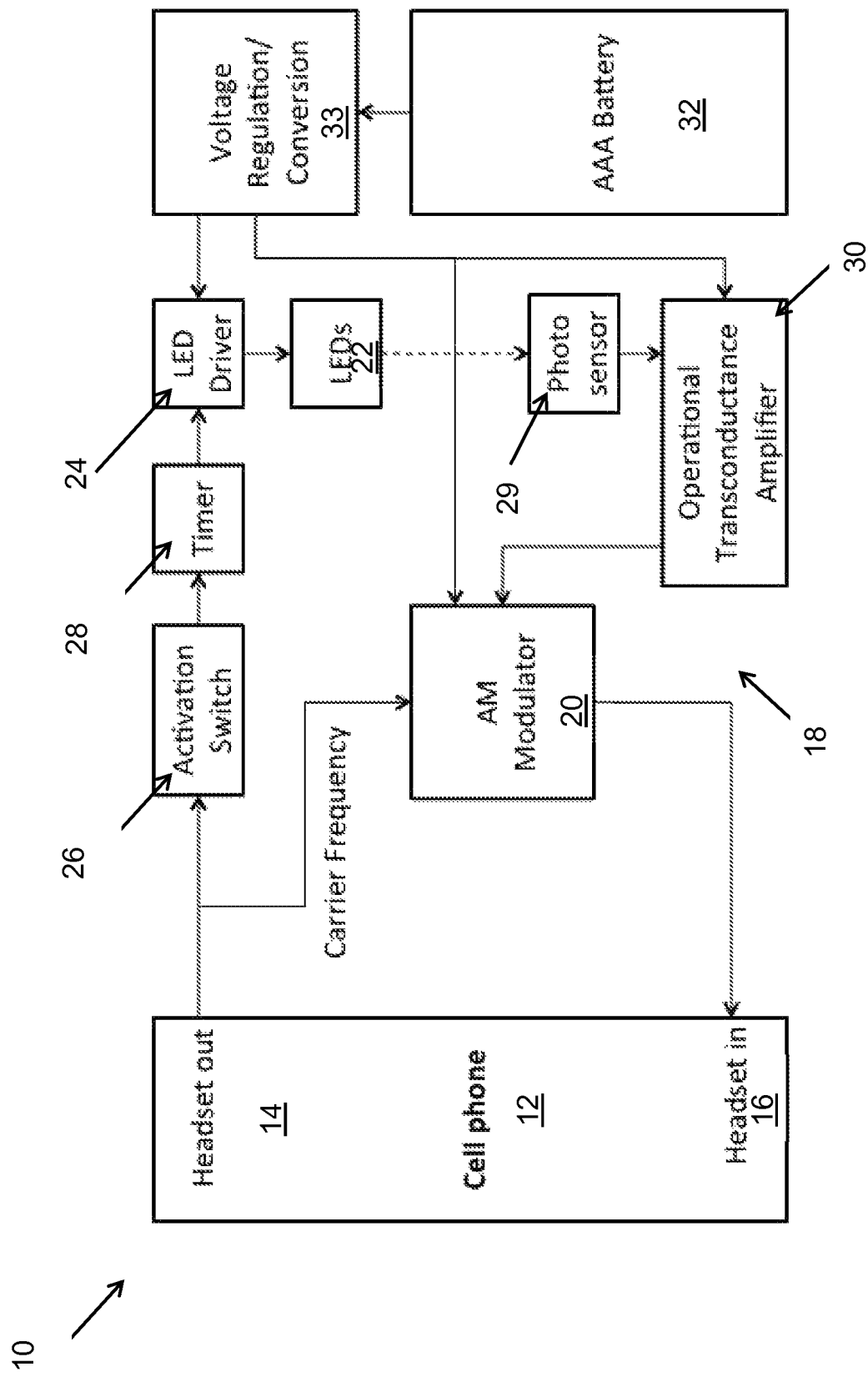
FIG. 1 illustrates a schematic diagram of a device for measuring hemoglobin in the blood, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a bio-fluid detector such as a hemoglobin detector having the capability of receiving, storing and transmitting health information utilizing a portable transmitter and receiver including electronic PDAs, such as cell phones. Further, the present invention utilizes a non-invasive hemoglobin detector that is connected to a portable transmitter-receiver such as PDAs including, but not limited to, cell phones.

The basic principle of optical hemoglobin detection is based upon spectroscopy, and the Beer-Lambert law:

$$I = I_{0,\lambda} e^{-\Sigma_i \varepsilon_{i,\lambda} * \delta * c_i}, \qquad (1)$$

$\varepsilon$=extinction coefficient of material i at wavelength $\lambda$,
$\delta$=path length of light,
$c_i$=concentration of material i,
$I_0$=incident light intensity,
$I$=transmitted light intensity According to equation (1), under ideal conditions the intensity of transmitted light through a solution can be related to its composition. Under laboratory conditions, hemolyzed blood is often accordingly analyzed at several wavelengths to determine precise concentrations of different types of hemoglobin; this is sometimes used to determine levels of carboxyhemoglobin in blood during postmortem investigation of fire or carbon monoxide related deaths.

Photoplethysmography purposes to acquire absorbance data from blood without the need for a blood sample. Light at specific wavelengths, in this case at the isosbestic wavelength for deoxy and oxyhemoglobin, 810 nm, is shone through tissue, often the finger or the earlobe, and the transmitted light is captured. During transmission, a portion of the light passes through the artery within the finger and is absorbed by hemoglobin within the blood. This blood absorption component varies with time according to the changing diameter of the artery during systole and diastole. Detectable in the intensity of transmitted light, therefore, is a pulsatile component whose magnitude is directly related to the magnitude of absorption of arterial blood.

One problem that arises in passing light through tissue is unpredictable scattering and absorption of light due to the heterogeneity of the tissue and the light path; this can be compensated by a ratiometric approach:

$$O.D_{810} \approx \frac{\frac{AC_{810}}{DC_{810}}}{\frac{AC_{ref}}{DC_{ref}}} \qquad (2)$$

O.D=optical density,
AC=the pulsatile component of the signal, in this case the peak to peak magnitude,
DC=the non-varying component of the signal Within the DC component of the denominator and numerator are component attributable to the thickness, opaqueness and geometry of the tissue, independent of the specific wavelength of light used; therefore, these components cancel out in (2), and what is left is a reliable measure of a ratio of AC's. Conveniently, if the denominator contains a reference wavelength independent of Hb, then the ratio becomes robust to fluctuations in blood volume and the reliability of the measure is increased.

The measure of interest is simply the optical density or the absorption due to blood in the artery at 810 nm. The magnitude of this density or absorption is intrinsically correlated to hemoglobin concentration, as hemoglobin is the major absorptive component of blood in the NIR range. The use of 810 nm light, for which the extinction coefficients of oxy- and deoxy-hemoglobin are equal, ensures a relationship unaffected by changing oxygenation levels between the total concentration of deoxy/oxyhemoglobin, together constituting 90-95% of normal blood hemoglobin content, and the absorption of 810 nm by blood. Thus, estimation of this absorption leads directly to an estimate of hemoglobin content.

One final caveat is that the scattering of light by disc-shaped whole blood cells introduces a small degree of non-linearity into the system. The Twersky equation (3) is an accepted characterization of this non-linear relationship. Importantly, in physical ranges, it has been shown that the relationship between hematocrit and light absorption is nearly linear; consequently, it can be argued that the relationship between hemoglobin concentration and absorption can be approximated as nearly linear in the physical range, especially if extreme accuracy is not a requirement, as in the present invention.

Twersky's equation:

$$O.D = \log_{10}\left(\frac{I_0}{I}\right) = \varepsilon\delta c - \log_{10}[10^{-a\delta h(1-h)} + q(1 - 10^{-a\delta h(1-h)})] \quad (3)$$

where ε, δ, c are the same as before,
a=constant dependent on size of RBCS, refractive index, and wavelength,
h=fractional hematocrit,
q=constant dependent on RBC size, refractive index, wavelength, and the aperture angle of the photodetector FIG. 1 illustrates a schematic diagram of a device for measuring hemoglobin in the blood, according to an embodiment of the present invention. As illustrated in FIG. 1, the device 10 includes a cellphone 12 having a headset-out sound transmitter 14 and a headset-in port 16. A sensor system 18 taking the form of a finger clip, not illustrated in the schematic diagram, is coupled to the cellphone 12 via the headset in port 16. The sensor system 18 includes a circuit board (not shown), referred to as a communication board, including a communication device 20 to transmit communication from the sensor system 18 to the cellphone 12. The sensor system 18 also includes an LED 22 and an LED driver 24. The LED driver 24 is coupled to an activation switch 26 and also a timer 28 in order to activate the LED for a hemoglobin reading. The LED 22 is used to transmit light to a photosensor 29 to determine the amount of the light transmitted from the LED through the tissue of the subject to the photosensor 29. The photosensor 29 transmits the light information to an operational transconductance amplifier 30 that is configured to transmit information about the light information to the cellphone 12. External battery power 32 can be used to power the system, rather than the more limited power that can be harnessed from the headset jack of the cellphone itself. A voltage regulation/conversion device 33, therefore, may also be needed. A completely cell-phone powered device also is possible with the utilization of low-power LEOs and circuitry.

The sensor system 18 can include a low-power, ultra-cheap sensor, in order to keep costs down for use in developing nations. The sensor system 18 plugs into and communicates with low-end cellphones 12 via the headset in port 16, a nearly universal feature on cell phones. Computation can be provided by an applet on the cellphone itself, and power either by a small battery or the cellphone itself. Computation can also be done on MATLAB on a laptop, using the computer's microphone and headphone jacks as stand-ins for a cellphone headset jack.

Figure 2:
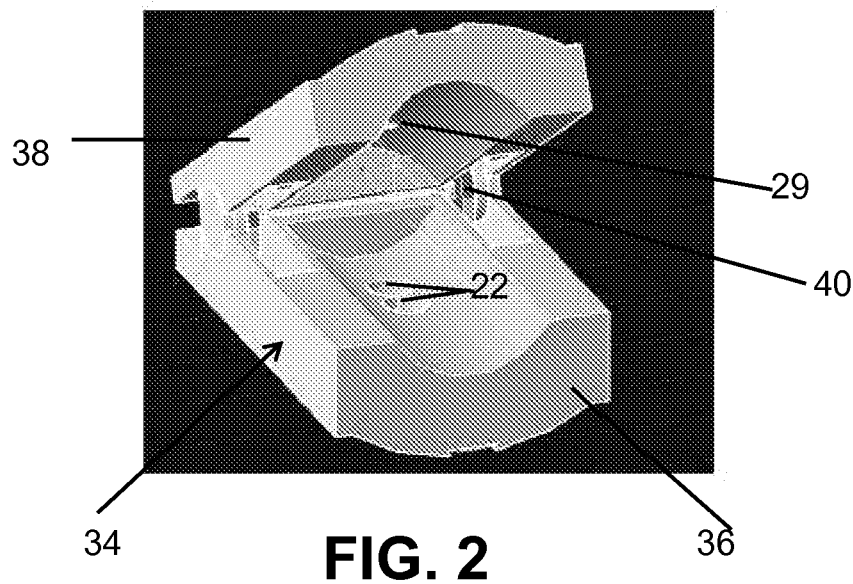
FIGS. 2 and 3 illustrate perspective views of the finger clip, according to an embodiment of the present invention.
Figure 3:
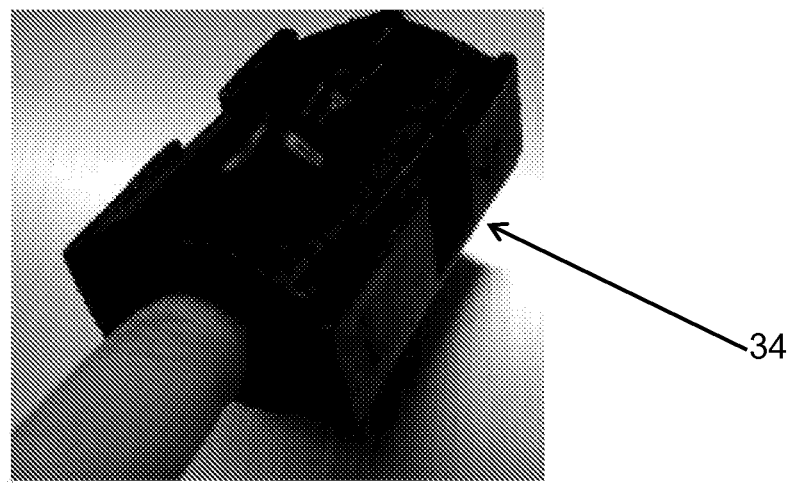

As discussed above with respect to FIG. 1, the sensor system 18 includes the circuit board and a finger clip containing two LED's 22 and the photosensor 29 or photodiode. FIGS. 2 and 3 illustrate perspective views of the finger clip, according to an embodiment of the present invention. The finger clip 34 includes a bottom piece 36 to hold the photosensor 29, a top piece 38 containing the LED's 22, and a torsion spring 40. The torsion spring 40 is configured to hold both the bottom piece 36 and the top piece 38 together, as well as keeping the clip clamped shut to reduce interference from external light. The entire finger clip 34 is preferably covered in matte black paint in order to reduce noise from the scattering and reflecting light insider the sensor.

The sensor system 18 also includes two LED's 22, at wavelengths 660 and 810 nm, shone through the finger, either index or middle, and collected by a photosensor 29. The 810 nm wavelength is the isosbestic point for deoxy- and oxy-hemoglobin; as such it is independent of oxygenation level. 660 nm was chosen for convenience, and based on previous work in literature. However, any number of LEDs producing any number of wavelengths of light could also be used.

Based on the Beer-Lambert law, the intensity of the light absorbed by the photosensors is related to the absorption of the substances within the medium through which the beam passes. Photoplethysmography is a method that uses this absorbance data to extract information specifically on the contents of the blood. Because arterial blood absorption increases and decreases, when there is a in blood volume during systole and diastole, within the resulting signal is a small pulsatile wave, called the plethysmograph. The properties of this pulsing signal, including amplitude and time variation, can be assumed to be related to changes in the arterial blood component only.

Figure 7:
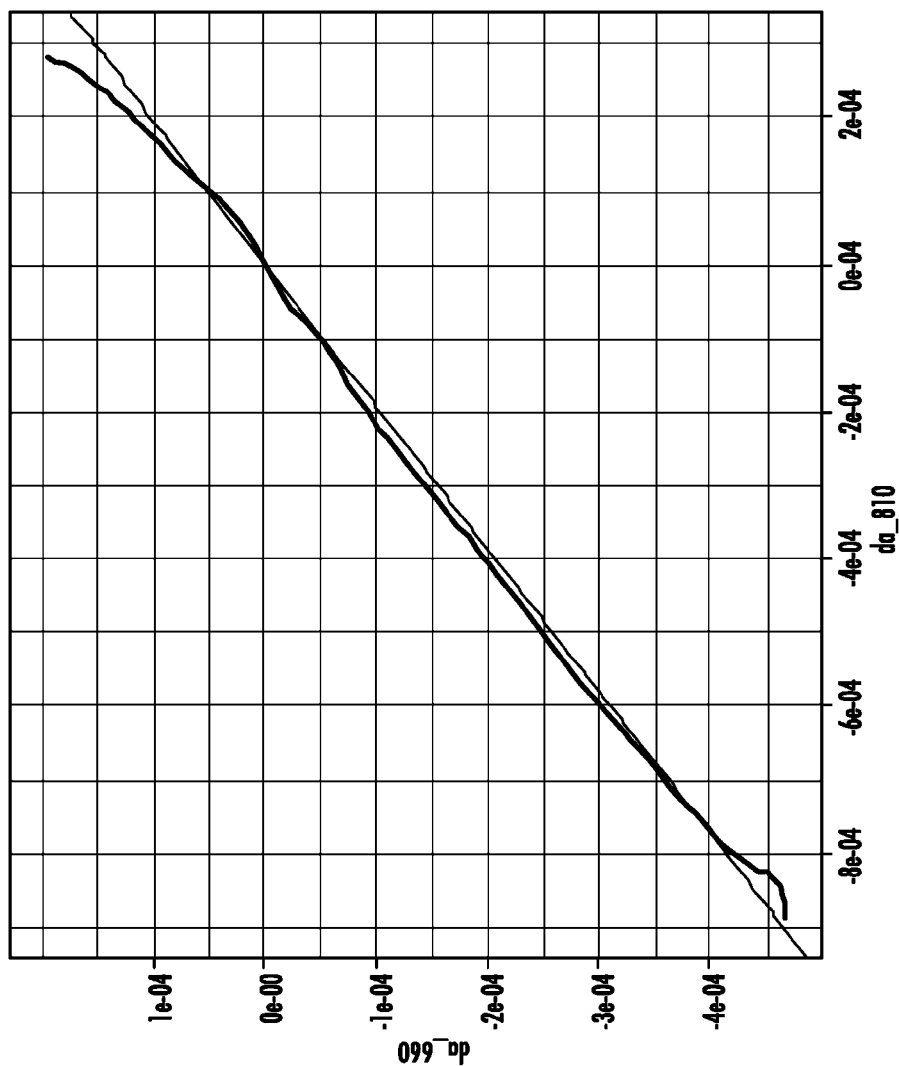
FIG. 7 illustrates a graphical view of the slope-correlation method, used according to an embodiment of the present invention.

When using light shone through tissue, there will be unpredictable scattering and reflection of light. In order to reduce the effect of the unpredictable scattering and reflection of light caused by components of tissue such as geometry and opacity, a ratiometric approach is used where the parametric slope of the time-derivatives of waveforms at two wavelengths is calculated. This method is roughly equivalent to the usual method of calculating a ratio of ratios of AC, or varying component, over DC, non-varying component, at two wavelengths used in pulse oximetry, but is expected to be more reliable under varying conditions, due to its use of a larger amount of the available information of a waveform, and its reliance on the ratios of time variance, rather than pure amplitude, of the waveforms. FIG. 7 illustrates a graphical view of the slope-correlation method, used according to an embodiment of the present invention. The slope of the linear interpolant of $dA_{\lambda,1}$ versus $dA_{\lambda,2}$ is the parametric slope or slope correlation method, represented by the equations reproduced below.

Represents the constant components of tissue $$DC_a = \boxed{f(r_a, r_f, \lambda)} DC, \quad DC = DC_a + DC_b$$

$$\Delta OD_{tot} = AC/DC_a = [1/f(r_a, R_f, \lambda)]AC/DC \equiv (1/f)/R$$

$$R_{ij} \equiv \frac{R_i}{R_j} = \frac{AC_i/DC_i}{AC_j/DC_j} = \frac{f(r_a, r_f, \lambda_i)\Delta OD_{tot,i}}{f(r_a, r_f, \lambda_j)\Delta QD_{tot,j}} \approx \frac{\Delta OD_{tot,i}}{\Delta OD_{tot,j}},$$

$$f(r_a, r_f, \lambda_i) \approx f(r_a, r_f, \lambda_j)$$

$$dA_\lambda = \frac{I_i - I_{i-1}}{(I_i + I_{i-1})/2},$$

The AC component contains information on the arterial blood while the DC component contains the absorption from the tissue shape and path. In order to obtain data for both wavelengths of light, the two lights need to be on at different times to obtain data for each specific wavelength. In the present invention, the pulse is recorded from one wavelength for 10 seconds, and then the LED's are switched manually and data is obtained from the second. The switching process can also be automated, through a frequency dependent switch controlled by tones played by the cellphone. Moreover, the LED's may eventually be pulsed at high rates using 555 timers, as in pulse oximetry; this has the advantage of reducing optical noise, and allows simultaneous, rather than sequential, collection of waveforms at 2 wavelengths, increasing the reliability of measures. Finally, because the present invention will measure a single value of Hb, rather than continuous values, as in pulse oximetry or commercial plethysmography based Hb-meters, from data that is averaged over time, the method can be expected to be more noise resistant. Further noise resistance can be conferred by the use of noise-identifying and rejecting methods (autocorrelation) for rejecting of aberrant pulses caused by motion artifacts or other sources of noise; this is not implemented in the current design.

Rejection of bad samples was done by judgment based on the waveforms during initial testing. There is also the issue of the differing average transmission of light from person to person caused by a variety of factors; someone might possibly saturate the photodiode, or oppositely not provide a strong enough signal. This problem is corrected using an auto gain control component, which tunes the voltage driving the LED's if the output average voltage is too high or too low, such that the DC voltage it levels off around a 2-2.5V region (out of a maximum operation range of 0-3.3V or 5V) where a pulse is visible. The gain control tuning takes from 2-8 seconds to stabilize. The device can be tuned manually using variable resistance trimpots.

Figure 4:
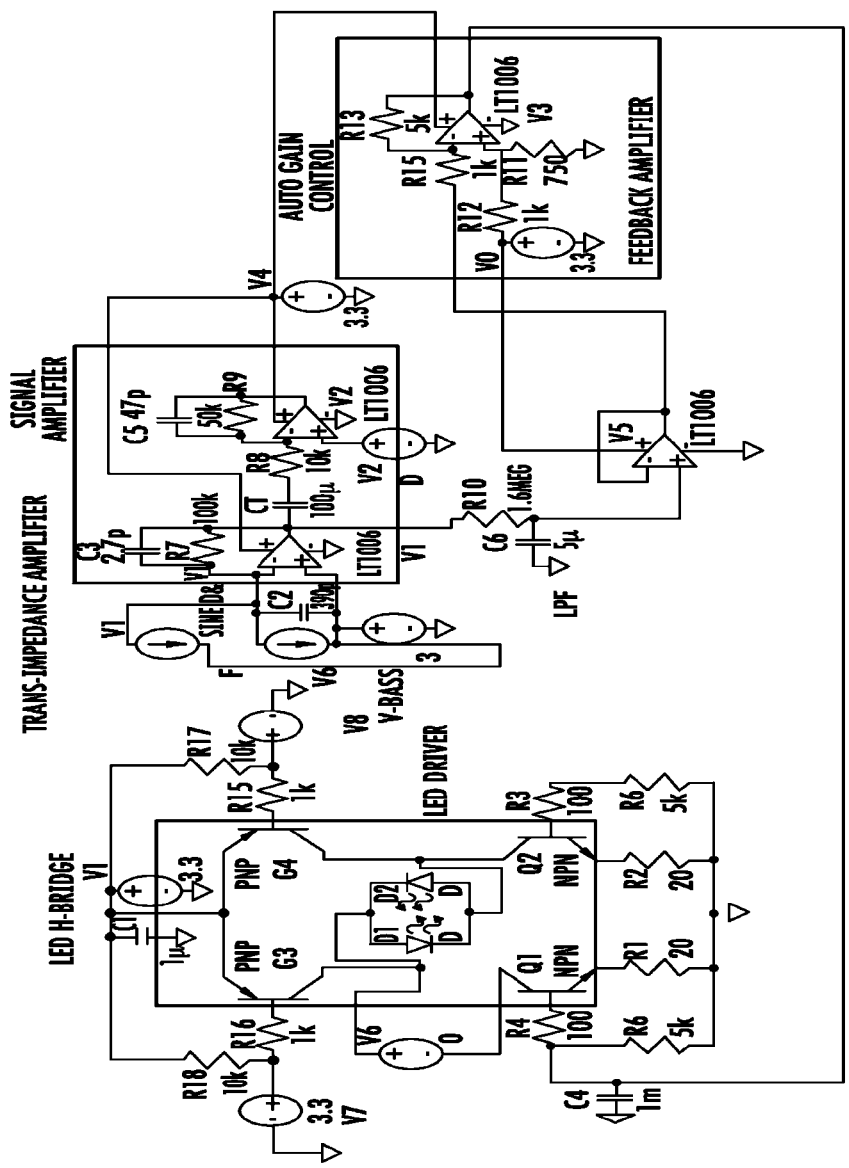
FIG. 4 illustrates a circuit diagram of a main sensor board, according to an embodiment of the present invention.

Another important aspect of the present invention is the communication board. FIG. 4 illustrates a circuit diagram of a main sensor board, according to an embodiment of the present invention. Preferably, the communication board can take the form of a separate, small, self-contained device that plugs into the cellphone via the headset jack and acts as communicator between various sensors—including the photosensor—and the cellphone. These sensors could also take the form of interchangeable peripherals. The versatility of such a device would be invaluable, allowing data of a large range of types to be collected and relayed remotely via cellphone; for example, soil and water pH, EKG readings, air pollution, among others. Two possible methods of communication can be used to implement the present invention. However, any other method of communication known to or conceivable by one of skill in the art could also be used. One such method is amplitude modulation (AM) and another such method is binary frequency shift keying (BFSK).

Figure 5:
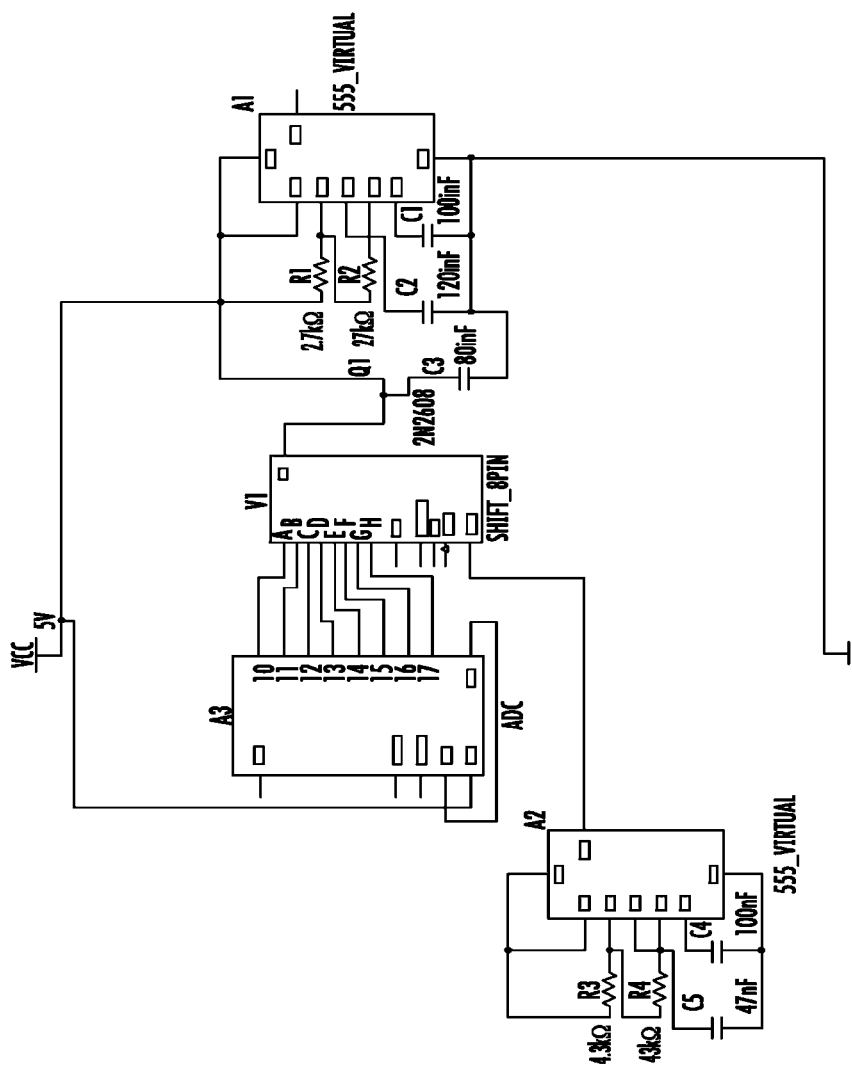
FIG. 5 illustrates an exemplary circuit diagram of a BFSK communication board according to an embodiment of the present invention.

FIG. 5 illustrates an exemplary circuit diagram of a BFSK communication board according to an embodiment of the present invention. BFSK is discussed herein as the preferable device for communication due to its versatility and noise resistance, and ability to transmit messages unchanged due to its digital nature. Amplitude modulation is simpler, but also potentially as difficult or more difficult to demodulate, and is subject to information loss and a narrow range of operation. The key constraint for any communication method is the fact that the cell phone audio jack is AC coupled, and therefore any signal passed to it must be of a frequency in the accepted range, approximately 300 Hz-3 kHz. Briefly, AM multiplies a low frequency signal with a carrier wave (sinusoidal) of high frequency. The resulting signal can be passed to the audio jack and demodulated within the phone by an envelope-detection algorithm.

One issue is that compression is done automatically by the phone when accessing the headset-in port. It may therefore be difficult to obtain a full spectrum waveform in pure form; low frequencies—i.e. the signal of interest—may be filtered out automatically by hardware within the phone in its attempt to isolate vocal harmonic frequencies for use in transmitting sparse voice information. On the other hand, if these specific frequencies are known, then a method using only one or two of them is at a significant advantage. BFSK is a simple digital communication method dating to the 1950's, when it was used by Bell 202 telephone modems; it simply represents binary 1 and 0 as two well-separated frequencies.

An efficient algorithm for calculating the power of presence of a specified frequency, Goertzel's algorithm, can then be used to decode the signal representing the bit-stream. By avoiding the calculation of fast Fourier transforms over all frequencies, the algorithm makes implementation of tone detection possible in a low computation setting—such as a low end cellphone. Conversion of a voltage signal to a digital signal is accomplished by an analog-digital converter (ADC). This digital signal is then encoded in BFSK by a specific circuit. The present invention is used in conjunction with a cell phone software application preferably coded in Java. Any other coding language or A pictorial display of anemia level can be provided for the healthcare worker via the GUI, and a numerical value can be logged and accessed. Further, the numerical hemoglobin value can be sent via SMS to a central server. A MATLAB script on a personal computing, tablet, or other computing can be used to acquire live data, display it, and analyze it afterwards.

A carrier frequency for amplitude modulation (AM) is provided by a tone played at a specific frequency by the phone, and outputted via the headset out channel. If a cellphone has stereo capability, two separate channels are available. If two channels are available, one may be used to either harvest power via a rectification and step up circuit, or to provide frequency based commands to the system, for example to a frequency dependent LED driver, wherein different frequencies cause a different LED to be turned on, similar to what occurs in a light organ. If a cellphone has only mono capability, this channel can be dedicated to the carrier frequency while signals are being transmitted. However, interceding data acquisition periods—during which a single LED will be on for a specified time and data recorded, this channel may be used temporarily to command the circuit to "switch" wavelengths, using a frequency dependent switch. This avoids the need for any kind of microcontroller on the external sensor board, maximizing what is done by the cell phone and minimizing the complexity and cost of the overall device.

The cellphone will thus be able to obtain the signals from the sensor by modulating the plethysmograph signal onto the carrier, and inputting the resulting waveform into the headset-in input of the headset jack. By AM, a signal can be represented by manipulating the amplitude of the carrier wave.

Given a carrier wave represented by the function:

$$c(t)=A_c \cos(w_c t+\varnothing_c)$$

Where $A_c$ is the amplitude, $\varnothing_c$ is the initial phase, and the frequency (Hz) of the wave can be expressed as we, and the signal to be expressed by the carrier wave is given by the function:

$$S(t)=A_s \sin(w_s t+\varnothing_s),$$

Where $A_s$ is the amplitude, $\varnothing_s$ is the initial phase, and the frequency (Hz) of the wave can be expressed as $$\frac{w_c}{2\pi},$$

and the signal to be expressed by the carrier wave is given by the function:

$$S(t)=A_s \sin(w_s t+\varnothing_s),$$

where $A_s$ is the amplitude, $\varnothing_s$ is the initial phase, and the frequency (Hz) of the wave can be expressed as $$\frac{w_s}{2\pi},$$

and the frequency of the carrier wave is much greater than the frequency of the signal, or $$\frac{w_c}{2\pi} \gg \frac{w_s}{2\pi},$$

the AM signal can be expressed as the product:

$$S_{modulated}(t)=[1+S(t)]*c(t)$$

AM is commonly used to transmit radio waves over long distances, and is a less noise-robust but simpler method than frequency modulation (FM). In this device, AM using a carrier wave in the vocal range (1-10 khz) is required for the cellphone's AC-coupled mic input to detect the signal. Once the AM signal has been captured by the cellphone, a computationally inexpensive envelope-detecting method will be used to extract the original signal, which involves finding the focal maximums of the AM signal. Given that the pulsatile signal is at a much lower frequency than the carrier, it is possible to retain almost all the information of the original signal.

Figure 6:
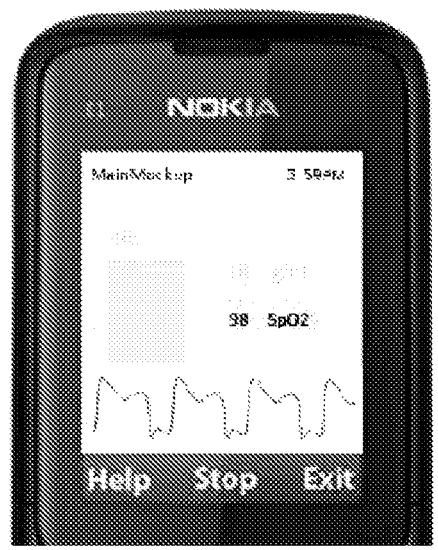
FIG. 6 illustrates an image of a cellphone displaying a signal, according to an embodiment of the present invention.

Thereafter, all calculations are performed by the applet on the cellphone. FIG. 6 illustrates an image of a cellphone displaying a signal, according to an embodiment of the present invention. The estimated hemoglobin concentration is converted into an easily interpreted visual icon on the graphical user interface on the cellphone screen. This icon can consist of a pictorial and/or a color expressing the anemic state of the patient. During the initialization of the device, the screen will display feedback to let the user know if the sensor is correctly connected, and if usable signals are being acquired from the patient. During data acquisition, a real time display of the plethysmograph waveform will be displayed in a portion of the screen, as illustrated in FIG. 6. At the same time, a menu system on the applet will allow the health worker to input the name and other important information. This information will be stored and eventually relayed, together with the hemoglobin reading and anemia status, via SMS to a permanent database. Importantly, this relaying of a message allows the location of the reading to be determined via cell phone tower locations, and documented. All of this information is invaluable to local health departments in public health planning, and tracking of critically anemic pregnant women for follow up care.

In another embodiment of the present invention, a single wavelength of light is used, 810 nm, rather than two. This will allow for an extremely simple sensor board comprising only of the LED and a light detection circuit, and the AM system.

Another embodiment of the present invention uses three wavelengths of light, two of which are the wavelengths commonly used in pulse oximetry, 660 nm (red) and 930 940 nm (IR), and 810 nm. This will allow the device to be used in addition as a pulse oximeter, and the cellphone applet will contain options to enable pulse oximetry and/or hemoglobin detection.

In another alternative embodiment of the present invention, frequency modulation (FM) is used rather than AM to communicate with the cellphone. In particular, binary frequency-shift-keying (BFSK) is a more noise-resistant, and still relatively simple method of communication using frequency. These frequencies will need to be generated on the sensor, requiring analog to digital conversion and increasing the complexity and cost of the device. However, the digitization of data allows a much greater variety of data to be transmitted, not just voltage. In addition, BFSK is more reliable, and ultimately more sensitive than AM for communicating data to the cellphone. BFSK consists of two tones, each representing a 1 or a 0. Decoding on the cell phone side can be done relatively cheaply, which in turn allows for higher transmission rates.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A sensor system, comprising:
a pair of light emitting diodes (LEDs) configured to:
    transmit light through tissue of a subject,
        wherein a first LED of the pair of LEDs is configured to emit light at 660 nm, and
        wherein a second LED of the pair of LEDs is configured to emit light at 810 nm;
an LED driver;
an activation switch configured to:
    activate the pair of LEDs, according to tones from a mobile communication device, via the LED driver to determine a hemoglobin level in a blood of the subject;

a timer coupled to the LED driver and the activation switch,
  the timer being configured to:
   receive a signal from the activation switch, and output a signal to the LED driver;
a photosensor configured to:
  receive and measure light transmitted through the tissue of the subject by the pair of LEDs;
a communications board configured to:
  trigger the pair of LEDs to transmit light,
  receive information related to light received by the photosensor, and
  receive the tones from the mobile communication device;
an operational transconductance amplifier configured to:
  transmit, to the mobile communication device and using binary frequency shift keying (BFSK), the information related to the light received by the photosensor; and
a housing, taking a form of a finger clip, configured to:
  hold the pair of LEDs, the photosensor, and the communications board.

2. The sensor system of claim 1, further comprising a power source for providing power to the sensor system.

3. The sensor system of claim 1, wherein the sensor system is further configured to:
receive power from the mobile communication device.

4. The sensor system of claim 3, wherein the power is received from a battery of the mobile communication device.

5. The sensor system of claim 1, wherein the communication board further comprises:
the operational transconductance amplifier.

6. The sensor system of claim 1, wherein the communications board is further configured to:
communicate with the mobile communication device via a headset jack of the mobile communication device.

7. The sensor system of claim 1, further comprising:
an analog-digital converter (ADC).

8. The sensor system of claim 1, wherein the sensor system is configured to:
receive power from an external battery.

9. The sensor system of claim 1, wherein the first LED and the second LED are activated at different times.

10. The sensor system of claim 1, further comprising:
an amplitude modulator to modulate the tones received from the mobile communication device.

11. A sensor system, comprising:
a finger clip configured to be disposed on a fingertip of a subject;
a light emitting diode (LED) configured to:
  activate according to tones from a mobile communication device, and
  transmit light through tissue of the subject,
   the LED being disposed on a first surface of the finger clip adjacent to the fingertip of the subject;
an LED driver;
an activation switch configured to: activate the LED, according to the tones from the mobile communication device, via the LED driver to determine a hemoglobin level in a blood of the subject;
a timer coupled to the LED driver and the activation switch, the timer being configured to:
  receive a signal from the activation switch, and output a signal to the LED driver;
a photosensor configured to:
  receive and measure light transmitted through the tissue of the subject by the LED,
  the photosensor being disposed on a second surface of the finger clip opposite the first surface of the finger clip; and
a communications board configured to:
  trigger the LED to transmit light,
  receive information related to light received by the photosensor; and
  transmit, to the mobile communication device, the information related to the light received by the photosensor.

12. The sensor system of claim 11, further comprising:
a power source for providing power to the sensor system.

13. The sensor system of claim 12, wherein the power source further comprises a battery.

14. The sensor system of claim 11 wherein the communication board further comprises:
an amplifier.

15. The sensor system of claim 14, wherein the amplifier is configured to perform binary frequency shift keying (BFSK) or amplitude modulation (AM).

16. The sensor system of claim 11, wherein the LED is a first LED; and
wherein the sensor system further comprises:
  a second LED configured to:
   transmit light through the tissue of the subject.

17. The sensor system of claim 16, wherein a wavelength of light emitted by the first LED comprises 660 nm; and
wherein a wavelength of light emitted by the second LED comprises 810 nm.

18. A sensor system, comprising:
a pair of light emitting diodes (LEDs) configured to:
  transmit light through tissue of a subject,
   wherein a first LED of the pair of LEDs is configured to emit light at 660 nm, and
   wherein a second LED of the pair of LEDs is configured to emit light at 810 nm;
an LED driver;
an activation switch configured to:
  activate the pair of LEDs, according to tones from a mobile communication device, via the LED driver to determine a hemoglobin level in a blood of the subject;
a timer coupled to the LED driver and the activation switch,
  the timer being configured to:
   receive a signal from the activation switch, and output a signal to the LED driver;
a photosensor configured to:
  receive and measure light transmitted through the tissue of the subject by the pair of LEDs;
a communications board configured to:
  trigger the pair of LEDs to transmit light,
  receive information related to light received by the photosensor, and
  receive the tones from the mobile communication device;
an operational transconductance amplifier configured to:
  transmit, to the mobile communication device and using amplitude modulation (AM), the information related to the light received by the photosensor; and
a housing, taking a form of a finger clip, configured to:
  hold the pair of LEDs, the photosensor, and the communications board.

19. The sensor system of claim 18, further comprising a power source for providing power to the sensor system.

20. The sensor system of claim 18, wherein the sensor system is further configured to:
  receive power from the mobile communication device.

\* \* \* \* \*